US010258301B2

(12) United States Patent
Rouet et al.

(10) Patent No.: US 10,258,301 B2
(45) Date of Patent: Apr. 16, 2019

(54) DIGITAL SUBTRACTION ANGIOGRAPHY (71) Applicant: KONINKLIJKE PHILIPS N.V., Eindhoven (NL)

(72) Inventors: Laurence Rouet, Paris (FR); Raoul Florent, Ville d'Avray (FR); Patrick Laurent, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/539,712

(22) PCT Filed: Dec. 24, 2015

(86) PCT No.: PCT/EP2015/081226
§ 371 (c)(1),
(2) Date: Jun. 26, 2017

(87) PCT Pub. No.: WO2016/110420
PCT Pub. Date: Jul. 14, 2016

(65) Prior Publication Data
US 2017/0347982 A1    Dec. 7, 2017

(30) Foreign Application Priority Data
Jan. 5, 2015 (EP) .................... 15305003

(51) Int. Cl.
*A61B 6/00* (2006.01)
*G06T 5/50* (2006.01)
*G06T 7/254* (2017.01)

(52) U.S. Cl.
CPC .......... *A61B 6/4441* (2013.01); *A61B 6/481* (2013.01); *A61B 6/504* (2013.01); *A61B 6/5264* (2013.01);
(Continued)

(58) Field of Classification Search
CPC ....... A61B 6/4441; A61B 6/481; A61B 6/504; A61B 6/5264; G06T 7/254; G06T 5/50;
(Continued)

(56) References Cited

U.S. PATENT DOCUMENTS 4,729,379 A    3/1988 Ohe
5,848,121 A   12/1998 Gupta
(Continued)

FOREIGN PATENT DOCUMENTS

DE    102006017098 A1    10/2006
DE    102006047719 A1    4/2008

OTHER PUBLICATIONS

Hiroshima, Kyoichi et al "Digital Subtraction Angiogram Registration Method with Local Distortion Vectors to Decrease Motion Artifact" Journal of Biomedical Informatics, vol. 34, 2001, pp. 182-194.
(Continued)

Primary Examiner — Brenda C Bernardi (57) ABSTRACT

Digital subtraction angiography is used to improve the contrast of images of patient vasculature. A non-contrast image is recorded with no contrast medium injected into the patient, and then a succession of contrast images is captured after the injection of a contrast medium. The non-contrast image is successively registered to the contrast images, and then subtracted. This removes background structures, but leaves the vasculature untouched, making blood vessels easier to see. Artifacts can remain when different motion layers are present in the X-ray image (for example, the spine and the lungs). This application discusses a technique to prevent artifacts occurring when different motion layers are present in an X-ray frame or sequence.

14 Claims, 5 Drawing Sheets (52) U.S. Cl.
CPC ............... *G06T 5/50* (2013.01); *G06T 7/254* (2017.01); *G06T 2207/10116* (2013.01); *G06T 2207/20224* (2013.01); *G06T 2207/30101* (2013.01)

(58) Field of Classification Search
CPC . G06T 2207/10116; G06T 2207/20224; G06T 2207/30101
See application file for complete search history.

(56) References Cited

U.S. PATENT DOCUMENTS

| | | | |
|---|---|---|---|
| 2007/0036269 | A1 | 2/2007 | Lienard |
| 2008/0037844 | A1 | 2/2008 | Baumgart |
| 2008/0085034 | A1 | 10/2008 | Hildebrandt |
| 2009/0010512 | A1* | 1/2009 | Zhu .................. A61B 6/481 382/130 |
| 2010/0034446 | A1 | 2/2010 | Zhu |
| 2011/0293162 | A1* | 12/2011 | Pajeau .................. G06T 5/50 382/132 |
| 2011/0305378 | A1* | 12/2011 | Florent .................. A61B 6/481 382/130 |
| 2012/0201439 | A1 | 8/2012 | Rauch |
| 2012/0321156 | A1* | 12/2012 | Waechter-Stehle .......... G06T 7/2053 382/130 |
| 2013/0094734 | A1* | 4/2013 | Rauch .................. G06T 7/38 382/130 |

OTHER PUBLICATIONS

Meijering, Erik H.W. et al "Retrospective Motion Correction in Digital Subtraction Angiography: A Review". IEEE Transactions on Medical Imaging, vol. 18, No. 1, Jan. 1999, pp. 2-21.

* cited by examiner

DIGITAL SUBTRACTION ANGIOGRAPHY

CROSS-REFERENCE TO PRIOR APPLICATIONS

This application is the U.S. National Phase application under 35 U.S.C. § 371 of International Application No. PCT/EP2015/081226, filed on Dec. 24, 2015, which claims the benefit of European Patent Application No. 15305003.4, filed on Jan. 5, 2015. These applications are hereby incorporated by reference herein.

FIELD OF THE INVENTION

The present invention relates to a device for providing a digital subtraction angiogram, a method for providing a digital subtraction angiogram, an X-ray imaging arrangement, a computer program element, and a computer-readable medium.

BACKGROUND OF THE INVENTION

Digital subtraction angiography (DSA) is an X-ray imaging method, which removes background structures from an X-ray image. A non-contrast image (mask image) containing the background structures is acquired from a patient. Then, a contrast medium is injected into the patient, and an X-ray image is made of blood vessels containing the contrast medium. The non-contrast image is subtracted from an X-ray image of the blood vessels with contrast agent injected. In this way, there is an improved contrast between blood vessels and their background. U.S. Pat. No. 4,729,379 discusses digital subtraction angiography. However, the DSA-technique has been shown to be less useful when there are a number of independent motions in the imaged region of interest of the patient. Techniques for providing DSA can, therefore, be further improved.

SUMMARY OF THE INVENTION

It would be advantageous to have an improved technique for providing digital subtraction angiography.

Towards this end, a first aspect of the invention provides a device for providing a digital subtraction angiogram, comprising:
an interface unit; and
a processing unit.

The interface unit is configured to provide a non-contrast frame for use as a mask image, and to provide a contrast frame. The non-contrast frame and the contrast frame are acquired from a frame sequence of a region of interest of a patient.

The processing unit is configured to generate a first compensated mask frame by compensating the non-contrast frame for motion occurring in a first layer of the region of interest; to subtract the first compensated mask frame from the contrast frame; to generate a second compensated mask frame by compensating the first compensated mask frame for motion occurring in a second layer of the region of interest; and to generate a subsequent image by subtracting the second compensated mask frame from the result of the subtraction of the first compensated mask frame from the contrast frame.

According to a second aspect of the invention, there is provided a method for providing a digital subtraction angiogram, comprising the following steps:

According to an aspect of the invention, there is provided a method for providing a digital subtraction angiogram, comprising the following steps:
a) providing a non-contrast frame for use as a mask image, and providing a contrast frame, wherein the non-contrast frame and the contrast frame are acquired from a frame sequence of a region of interest of a patient;
b) generating a first compensated mask frame by compensating the non-contrast frame for motion occurring in a first layer of the region of interest;
c) subtracting the first compensated mask frame from the contrast frame;
d) generating a second compensated mask frame by compensating the first compensated mask frame for motion occurring in a second layer of the region of interest;
e) generating a subsequent image by subtracting the second compensated mask frame from the result of the subtraction of the first compensated mask frame from the contrast frame.

According to a third aspect of the invention, there is provided an X-ray imaging arrangement comprising:
an X-ray acquisition device with an X-ray source and an X-ray detector;
a device for providing a digital subtraction algorithm according to one of the preceding claims; and
a display device;
wherein the X-ray imaging arrangement is configured to acquire X-ray image data of a region of interest of a patient, and to provide the X-ray image data to the interface of the device for providing a digital subtraction angiogram, and to display the digital subtraction angiogram on the display device.

According to a fourth aspect of the invention, there is provided a computer program element for controlling a device according to the first aspect, which, when the computer program element is executed by a processing unit, is adapted to form the method steps according to the second aspect.

According to a fifth aspect of the invention, there is provided a computer-readable medium having stored the computer program element of the fourth aspect.

Advantageously, a device, method, X-ray system, computer program element, and/or computer-readable medium according to the previous aspects artefacts are reduced or removed that are remaining in digital subtraction angiogram images in conditions where the X-ray image is being acquired through at least two transparent layers inside a patient, and the layers move independently of each other to some degree.

It is noted that X-ray images are transparency images, and the superposed movement of at least two layers is a complicated function resulting from the superposition of various motion layers with different characteristics. It is, therefore, difficult to compensate accurately all sources of motion. A combined motion caused by the superposition of two motion layers is difficult to correct because there is a mixing of different deformations, each with different transparency and biomechanical characteristics.

For example, a rigid deformation of a rib bone, and a non-rigid deformation of a lung lobe could be mixed in the same contrast image.

There may be variable motion amplitudes for different structures. Rigid background structures, for example the spinal column, will usually have a very small amplitude of motion. Structures related to breathing or cardiac motion may have a larger amplitude of motion. According to aspects the present invention, it is possible to compensate for such separate sources of motion in a DSA image or sequence, even if they initially appear as superposed motion layers.

Advantageously, the algorithm also enables the application of different suitable registration algorithms to different motion layers.

In the present invention, the term "X-ray image sequence" means a plurality of frames each containing an X-ray image of a region of interest of a patient under examination. The frames may be acquired in an exposure mode, which allow the acquisition of an X-ray image or sequence, containing a number of contrast images. The sequence can contain frames acquired before the injection of a contrast agent, which are referred to as non-contrast frames (mask frames). After a contrast agent is injected into the region of interest, frames in the X-ray image sequence form contrast frames, showing more clearly the presence of blood vessels in the region of interest. Of course, after a certain period, the contrast agent will dissipate into the vasculature, and it will again be possible to acquire non-contrast frames.

The term "first layer of the region of interest" or "second layer of the region of interest" refers to different entities, or motion domains, inside the body of a patient. For example, the first layer of the region of interest could be formed from bone, in the case of a rib cage or a spinal column of the patient. The second layer of the region of interest could be formed from a layer containing the lungs. Many other variations will occur to the skilled person. It will be appreciated that because the term first layer and second layer apply to different organs or structures in a body, the motion of the first layer will often be different to the motion of the second layer, owing to biomechanical differences between them. They could also appear to have a different appearance in the X-ray image.

The term "geometrical transform" refers to a mathematical operation applied to a frame of an X-ray image sequence. A mathematical operation may be a translation, a rotation, an affine transform, an elastic warping, a stretching, or another form of transformation.

The term "similar in layer image content" means that two X-ray frames or images, or arbitrary regions of them, will have a similarity in the distribution of intensity, gradient, pattern, texture, contour, noise-figure, or in the location of shapes. In other words, two frames having similar layer image content are approximately identical to each other.

An aspect of the invention is, therefore, that multiple motion layers in a region of interest of a patient are separated using a multiple subtraction approach. A first subtraction is performed in combination with a first motion compensation, in order to remove a first structure, for example, static structures like bone. Then, a second subtraction is applied on the result of the first subtraction with a variable mask adapted to minimize or to compensate, for example, breathing structures (such as the diaphragm). Therefore, separate sources of motion may be compensated, for even if they appear to be superposed motion layers. The technique can be extended to situations where three, four or more motion layers are present, provided that the necessary subsequent subtractions and mask estimation steps are provided.

It is to be understood that the invention is not limited to the compensation for two motion layers. In the method discussed above, further stages of the algorithm may be applied, compensating for further different motion layers, before the display step is executed.

These and other aspects of the present invention will become apparent from and be elucidated with reference to the embodiments described hereinafter.

BRIEF DESCRIPTION OF THE DRAWINGS

Exemplary embodiments of the invention will be described with reference to the following drawings.

DETAILED DESCRIPTION OF EMBODIMENTS

Digital subtraction angiography (DSA) is an X-ray imaging modality, which can be used to study problems with blood flow, for example. During the DSA procedure, a contrast agent is injected into a patient's vasculature. Simultaneously, an X-ray source transmits X-ray radiation through a region of interest of a patient. An X-ray detector records an angiographic (X-ray) image sequence of the region that the contrast agent has been injected into, before, and at the same time that, the contrast agent propagates throughout the patient's vasculature. Such diagnostic angiograms permit the diagnosis of vascular diseases.

X-ray imaging relies on the transparency of a patient's tissue to X-rays. The intensity of an X-ray received at an X-ray detector, on the opposite side of a patient to an X-ray transmitter, will vary in a spatial distribution, dependent on the density of the structures in the patient that the X-ray has propagated through. The human body is composed of bone, and different types of tissue, all having different densities and biomechanical characteristics.

Different structures and tissue formations inside the patient can be stationary, or substantially stationary, whilst others move independently of each other. For example, a spinal column will appear to be substantially stationary, but a region corresponding to lung tissue lying on top of the spinal column will appear to move as the patient breathes.

Therefore, the X-ray image generated by the X-ray detector on the detector side of a patient is, in fact, a complex function of the state of the imaged region of interest of the patient. It is reliant on, for example, the patient's heart phase, their breathing phase, movements in their bowels, or on other movements applied to the patient externally, such as a rotation of an imaging table that the patient is supported on, or involuntary patient movement. It will be appreciated that the movements owing to breathing and heart processes are only weakly correlated within the time-frame of a DSA capture cycle.

This fact is detrimental to the application of digital subtraction angiography (DSA). DSA operates by capturing a non-contrast frame of a region of interest of a patient before a contrast medium is injected. The captured non-contrast frame contains traces of the background structure of the patient, for example, bones and other tissue, but it does not contain any significant traces of the patient's vasculature. Then, application of a DSA protocol captures a succession of contrast frames after the injection of the contrast medium into the region of interest. The patient's vasculature is somewhat visible in the contrast image owing to the absorption of X-rays by the contrast agent in the patient's bloodstream. However, the contrast image is often unclear.

Therefore, a non-contrast frame (mask frame) is subtracted from successive contrast frames. Traces in the X-ray image caused by bone and soft tissue are removed from successive contrast frames. Because the vasculature contains contrast agent that is not present in the non-contrast frame, a trace of the vasculature remains in the contrast image sequence after the non-contrast frame has been subtracted from the contrast image frames. DSA therefore removes unwanted background structures from an X-ray image frame.

When the bone and soft tissue structures in the contrast image sequence are offset, in relation to the same bone and soft tissue structures in the non-contrast frame, the subtraction of the non-contrast frame will cause artefacts to appear in the DSA images. This is detrimental to the diagnostic use of a DSA image sequence, because the artefacts do not represent real structural information about the patient. This situation is made more complicated when different portions of the region of interest of the patient move at different rates. It could be considered, for example, that when imaging a patient's thorax, the spinal structure is relatively rigid and still. The lungs are relatively elastic, and move with a higher amplitude. There is only a very weak correlation between the motion of the spinal structure, and the lungs.

When DSA is applied in such a situation, the artefacts remaining in the contrast images are complex, because the independent motion of the spine and lung tissue in the contrast images will be even more different from the non-contrast frame. Therefore an improved way of removing artefacts from DSA-images is required.

According to an aspect of the invention, there is provided a method for providing a digital subtraction angiogram, comprising the following steps:
a) providing a non-contrast frame for use as a mask image, and providing a contrast frame, wherein the non-contrast frame and the contrast frame are acquired from a frame sequence of a region of interest of a patient;
b) generating a first compensated mask frame by compensating the non-contrast frame for motion occurring in a first layer of the region of interest;
c) subtracting the first compensated mask frame from the contrast frame;
d) generating a second compensated mask frame by compensating the first compensated mask frame for motion occurring in a second layer of the region of interest;
e) generating a subsequent image by subtracting the second compensated mask frame from the result of the subtraction of the first compensated mask frame from the contrast frame.

Figure 1:
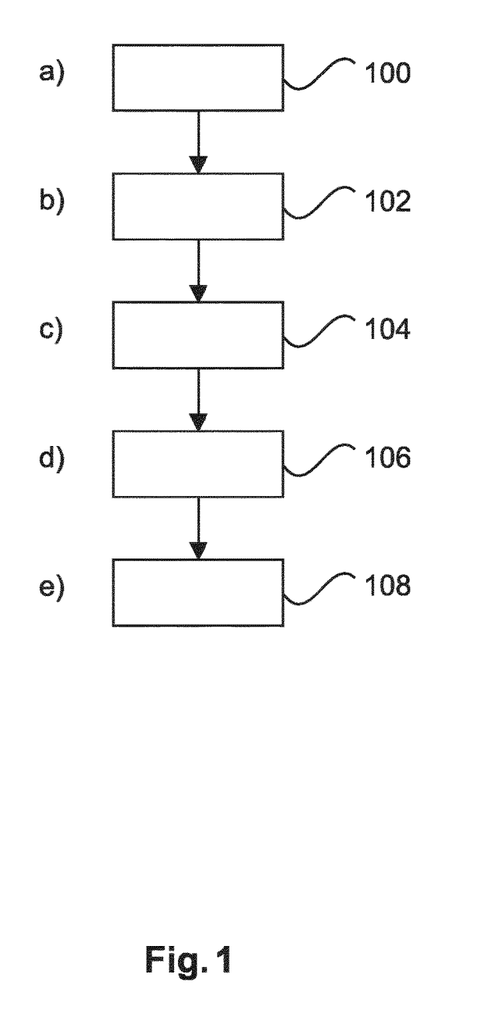
FIG. 1 shows a method according to an aspect of the invention.

FIG. 1 illustrates the method according to an aspect of the invention. An algorithm according to the method discussed above uses at least two subtractions. The first subtraction in step c) removes motion in a first layer of the region of interest occurring in the time between the acquisition of the plurality of non-contrast frame frames $I_M$ and the plurality of contrast frames $I_C$. The second subtraction, in step e), removes motion in a second layer of the region of interest occurring in the time between the acquisition of the plurality of non-contrast frames $I_M$ and the plurality of contrast frames $I_C$.

Therefore, it is possible to remove artefacts in an X-ray image resulting from the movement of at least two independently moving motion layers in an X-ray transparent medium. Of course, "independently moving" refers to relative motion between the motion layers, and one motion layer (representing a spinal column, for example) can be still, or substantially still.

A typical clinical protocol comprises obtaining a short X-ray sequence of the region of interest when no contrast agent is injected into the region of interest, to provide the plurality of non-contrast frames $I_M$. Then, a clinician injects a contrast agent into the region of interest. An image sequence obtained of the region of interest by an X-ray detector, such as a fluoroscope, during the contrast injection phase are referred to as the or contrast frames $I_C$.

During a typical application of the protocol, sequences of non-contrast frames and contrast frames are obtained in rapid succession. In the following, the X-ray image sequence is denoted as I. The X-ray image sequence has the plurality of non-contrast frame, $I_M$, and the plurality of contrast frames, $I_C$. These sections of the X-ray image sequence can be identified automatically, by image processing techniques, or by direct user input. Optionally, a further plurality of non-contrast frames may be obtained after the injection of a contrast agent, once the residual contrast agent has been cleared from the vasculature.

The overall architecture of the algorithm is, for each contrast frame of the X-ray image sequence I, to compensate for the motion of first layer in the region of interest, by generating the first compensated mask frame $MA_{t0}$ using an estimated motion vector field between a current contrast frame and a non-contrast frame. Then, the first compensated mask frame is subtracted from the current non-contrast frame. This forms a first subtraction, and results in an intermediate frame $A_t$ of an intermediate image sequence. In a second subtraction, a motion due to motion of a second layer of the region of interest is compensated in the subtracted domain. The subtracted second compensated mask frame $MB_{t1}$ is warped using the estimated motion in the second layer of the region of interest. Again, the estimated motion in the second layer of the region of interest is provided by using an estimated motion vector field between the current "first-subtracted" contrast frame, and a non-contrast frame used as a mask in the second subtraction. Then, the subtracted mask is subtracted from the current subtracted frame. Finally, the DSA-result is displayed.

It is noted that it is not essential that the non-contrast frame used for the first subtraction has an identical frame index to the subtracted non-contrast frame used for the second subtraction. Owing to the differences of the motion characteristics of different layers, it might be that, when correcting a second motion layer, an earlier or a later non-contrast frame might be more suitable for acting as a basis for a mask image than one with the same index as used for a first subtraction.

In step b), the first compensated mask frame $MA_{t0}$ is generated by compensating for motion between the contrast frame $I_t$ being calculated, and a non-contrast frame $I_{Mt0}$. The motion vector field of the first layer of the first contrast frame in relation to the mask frame is estimated. Then, the mask frame $I_{Mt0}$, is warped using the estimated motion vector field estimated between the first contrast frame $I_t$ and the non-contrast frame $I_{Mt0}$. This generates the first compensated mask frame $MA_{t0}$.

In an example, the motion in the first layer of the region of interest is due to a minor movement of a rigid structure, such as the rib cage or the spine of a patient.

In step c), the previously generated first compensated mask frame $MA_{t0}$ is subtracted from the first contrast frame (in other words, a current frame being processed by the DSA algorithm) of the plurality of contrast frames $I_C$.

In an example, the subtraction is a log-subtraction.

In other words, this first subtraction derives the intermediate frame $A_t$ of the intermediate image sequence A. The intermediate frame is a frame, in which the motion in the first layer of the region of interest has been removed.

In step d), structures in second layer of the region of interest are removed. The intermediate frame $A_t$ of the intermediate image sequence A is selected, which has a similar layer image content to the second layer of the region of interest.

This intermediate frame $A_{t1}$ may have the same X-ray image sequence index as that of the first compensated mask frame, or it may have a different index. This is because the process of generating the first compensated mask frame is independent from the process of generating a second compensated mask frame. The first compensated mask frame is derived from a frame of the X-ray image sequence I, and the second compensated mask frame is assembled from a frame of the intermediate image sequence A.

It will be appreciated that although this method derives one frame of the intermediate image sequence, the successive application of method on a frame-by-frame basis will result in the derivation of a succession of the intermediate image sequence frames A.

After selecting an intermediate frame $A_{t1}$ of the intermediate image sequence A, a subtracted mask frame $A_M$ is warped using the estimated motion vector field between the second layer of the region of interest of the intermediate frame $A_{t1}$ and the subtracted mask frame $A_M$.

The second compensated mask frame $MB_{t1}$ is generated thereby. The second compensated mask frame $MB_{t1}$ compensates for motion occurring in the second layer of the region of interest, wherein the motion in the second layer occurs in the time between the acquisition of the plurality of non-contrast frames $I_M$ and the variety of contrast frames $I_C$.

In step e), the second compensated mask frame $MB_{t1}$ is subtracted from the intermediate frame $A_{t1}$ of the intermediate image sequence A. This results in a subsequent image $B_t$. The subsequent image $B_t$ is an image with motion in the first layer removed in the first subtraction, and motion in the second layer removed in second subtraction.

According to an embodiment of the invention, in a further step f), the subsequent image $B_t$ is displayed.

It will be appreciated that the display of the subsequent image could be via a computer screen, television monitor, or alternatively the display of the image could be transmitted over a computer network or audiovisual distribution system to another display, or means.

According to an embodiment of the invention, a third subtraction process can be provided instead of displaying the subsequent image $B_t$. In other words, the derived subsequent image $B_t$ forms a frame of a second intermediate image sequence B. A third compensated mask frame is generated, after selection of a frame from the second intermediate image sequence. The third compensated mask frame compensates for a motion of a third layer in the region of interest. The motion in the third layer occurs in the time between the acquisition of the plurality of non-contrast frames $I_M$ and the plurality of contrast frames $I_C$.

Likewise, the algorithm may extend to a fourth, fifth, sixth, and more layers of the region of interest, dependent on the number of motion layers to be removed.

Viewed another way, the algorithm recursively removes different motion layers (motion domains) in the region of interest.

It will be understood that such recursions will occur in-between step e) and f) above.

Notably, the process of generating the first compensated mask frame in step b), and the step generating the second compensated mask frame in step c), does not require the same mask frame generation algorithm to be used. Therefore, the mask frame generation in each recursion of the algorithm may be optimized to the type of tissue expected in each layer of the region of interest. This may be extended to a third, fourth, fifth, sixth, and more layers.

In an example, the first layer of the region of interest may be relatively rigid, such as a spinal column. The motion in the second layer may be due to the motion of the lungs during breathing. The relatively rigid structure of the spinal column, and the generation of the first compensated mask frame might only require an identity transformation. There will be almost zero motion of the spinal column, and so substantially zero registration would be required between the non-contrast frame and the first contrast frame $I_t$. Motion in the second layer caused by a breathing motion would be better captured by an elastic registration algorithm or a vertical translation.

Therefore, according to an embodiment of the invention, a method is provided wherein the generation of the first compensated mask frame $MA_{t0}$, and the generation of the second compensated mask frame $MB_{t1}$ each uses a different algorithm, wherein each algorithm is specific to the first or second layer.

According to an embodiment of the invention, a method as previously described is provided, wherein first layer of the region of interest is a rigid layer. A rigid layer may refer to a bone structure such as the rib cage, the spinal column, a skull, a pelvis, and other areas containing bone.

According to an embodiment of the invention, a method is provided as described above, wherein the second layer of the region of interest is a tissue layer, which moves in synchrony with a patient's breathing, or a patient's cardiac motion, or a patient's bowel motion.

Figure 2:
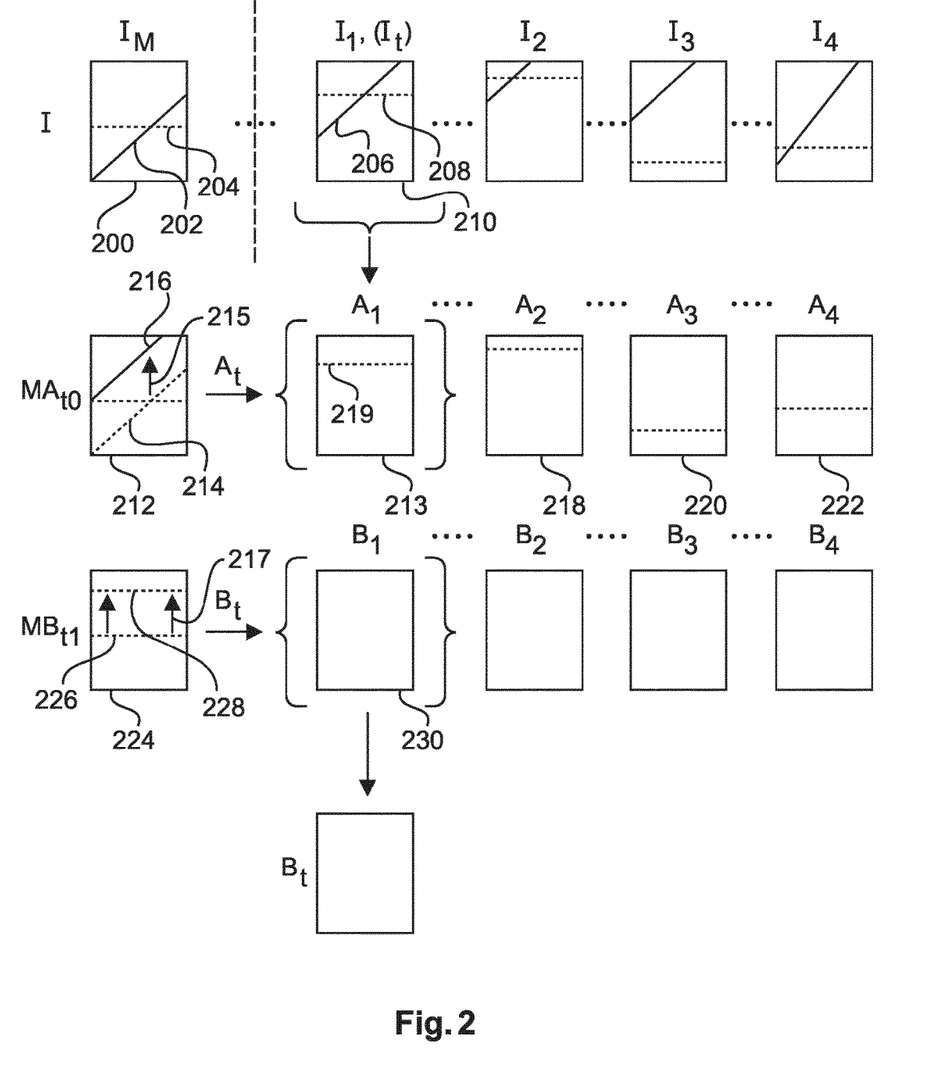
FIG. 2 shows a schematic representation of the processing of frames.

FIG. 2 illustrates the operation of the method diagrammatically. The frames of an input X-ray image sequence of the region of interest are shown in the top row of rectangular frames. Lower frame rows show the algorithm in operation.

In a frame 200 there is a solid line 202 crossing the rectangle of the frame 200 diagonally, and a dotted line 204 crossing horizontally. The diagonal solid line 202 represents the motion of a first layer of the region of interest. The horizontal dotted line 204 represents the motion of a second layer of the region of interest. To show that the layers are independent, in the succeeding frames on row I, it can be seen that the diagonal solid line 202 moves independently of the horizontal dotted line 204. The diagonal solid line 202 could represent a diaphragm position, and the horizontal dotted line 204 could represent the position of tissues around the heart, for example, because such layers are relatively independent over the duration of a DSA capture sequence.

A top left frame, indicated with the reference $I_M$, represents a non-contrast frame of the plurality of non-contrast frames. Therefore, this would not contain traces of a contrast agent. A sequence $I_1$, $I_2$, $I_3$, and $I_4$ represents contrast frames, in which contrast medium would be injected, although to aid the clarity of the drawings, the contrast medium is not shown.

FIG. 2 illustrates the conversion of one frame of a DSA sequence. It is to be understood that the algorithm would be applied in succession to $I_2$, $I_3$, and $I_4$, and successive frames, to provide a DSA image sequence.

A first contrast frame of the plurality of contrast frames, indicated with the reference $I_t$, is selected for conversion into an identical subtraction angiogram. The remaining discussion of FIG. 2 is explained in relation to the processing of this frame. A diaphragm line 206 and a cardiac line 208 in frame $I_1$ ($I_t$) are different to the positions of a diaphragm line, which is the solid line 202, and the cardiac line, which is the horizontal dotted line 204, in the non-contrast frame image $I_M$.

When generating the first compensated mask frame $MA_{t0}$ from the X-ray image sequence, one contrast frame is identified in the sequence of contrast frames $I_1, I_2, I_3,$ and $I_4$, in which the first layer of the region of interest has the closest, or a similar form, to the non-contrast frame (mask image). Therefore, in FIG. 2, the frame $I_1$ is selected as the most similar frame. A motion vector field 215 of a first layer between 210 and frame 200 is generated. Then, a warping operation is applied to the first motion layer of frame $I_1$, using the first motion vector field.

As shown in a frame 212, diaphragm position in the non-contrast frame has moved from its original position denoted by a diagonal dotted line 214 to a final position denoted by a diagonal solid line 216. It will be seen, therefore, that the warped mask frame has a diaphragm position, which is now the same as the position of the diaphragm 206 in frame $I_1$. Therefore, a first compensated mask frame 212 (also referred to with reference $MA_{t0}$) has been generated.

The first compensated mask frame $MA_{t0}$ is then subtracted from the first contrast frame of the plurality of contrast frames (in other words, the current contrast frame of the digital subtraction angiogram).

The result of this is shown in frame 213. The frame 213 is the intermediate frame $A_t$ of the intermediate image sequence A, of which $A_2, A_3,$ and $A_4$ are also members. As can be seen, the frame $A_1$ 213 does not have the diagonal diaphragm line because motion in the first layer of the region of interest was removed by first subtraction. A horizontal line 219 (corresponding to 208) is a residual artefact of the cardiac line in $A_1, A_2, A_3,$ and $A_4$. If not treated further, this would still cause a motion artefact to appear in the final (subsequent) image $B_t$.

For convenience, the frames 218 to 222 ($A_2, A_3,$ and $A_4$) in the intermediate image sequence A have also been shown with their original diagonal diaphragm lines removed, although it will be appreciated that a successive operation of the algorithm on the three remaining frames of the X-ray input sequence achieves this.

Turning to the removal of the second layer of the region of interest, the second compensated mask frame $MB_{t1}$ is generated by searching the intermediate image sequence A for the intermediate frame $A_{t1}$, which has a similar layer image content to a current frame.

Once this frame is identified, a second motion vector field 217 between $A_{t1}$ and $MA_{t0}$ is identified. The second layer in the first subtracted mask frame is warped, using the second motion vector field 217.

In FIG. 2 it can be seen that in a frame $MB_{t1}$, also referred with reference 224, the initial position of the horizontal dotted line, indicated with reference 226, is registered upwards to a position 228, reflecting the position of the second motion layer 218 in the intermediate image sequence frame $A_1$. Although, in this example, the registration of the second layer of the region of interest in the frame 224 is based on the same frame index as in the first iteration of the algorithm, it is to be understood that the two iterations are independent. If a more suitable position of the second layer of the region of interest (compared with $MA_{t0}$) is found, for example, in image $A_2, A_3,$ or $A_4$, this could also be used for the second registration of the intermediate mask frame 212.

After generating the second compensated mask frame $MB_{t1}$, i.e. the frame 224, it is subtracted from the intermediate frame $A_1$ resulting in subsequent image frame $B_1$ denoted 230. $B_1$ is illustrated as having no lines inside, which indicates that the motion artefacts resulting from the independent movement of the motion in a first layer of the region of interest, and the motion in a second layer of the region of interest, have been fully removed. Therefore, only traces of vascular structures containing contrast medium will remain in this image. It will be appreciated that a successive application of the algorithm to the frames in I will allow the calculation of frames $B_2, B_3,$ and $B_4$.

Although this schematic discussion of the algorithm has dealt with two iterations of the algorithm, third, fourth, fifth, sixth, or more iterations may be provided, if there are additional independent motion layers in the region of interest, which should be removed.

Different registration algorithms may be used in different stages. In this example, the motion of the diaphragm, i.e. the diaphragm line 206, is relatively predictable, and so a parametric registration algorithm may be applied to it. The motion of the second layer resulting from cardiac tissue movement may be more diffuse, and so an elastic (non-rigid) registration algorithm may be used to estimate the motion vector field in that iteration.

Figure 3:
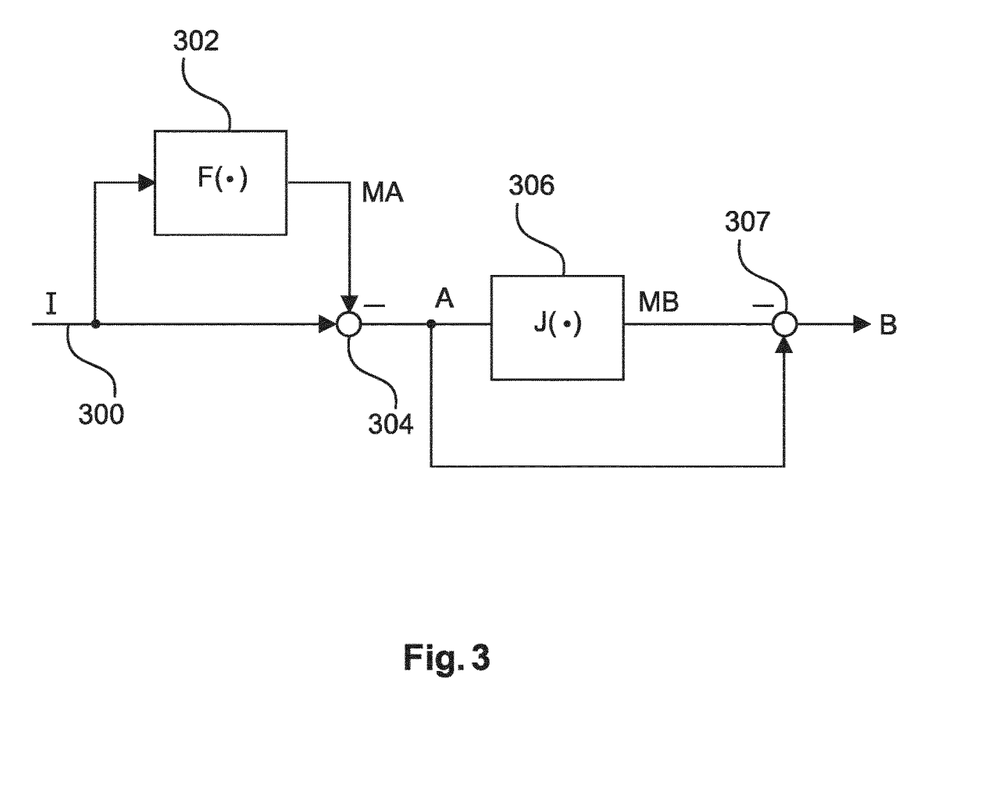
FIG. 3 shows an algorithm architecture.

FIG. 3 shows an algorithmic representation of the method according to an aspect of the invention. The X-ray image sequence I is input at an input 300. The sequence of first compensated mask frames MA is generated using a compensation unit 302 (or first compensator), which applies a first registration transform F(.).

Consequently, a first subtraction unit 304 (or subtractor) subtracts the first compensated mask frame MA from the X-ray image sequence I. The result of this is used as the intermediate image sequence A, which is also the input to a second compensation unit 306 (or second compensator).

The second compensation unit applies a second registration transform J(.).

It will be noted that in an embodiment, the registration transforms in the first compensation unit 302 and the second compensation unit 306 are different, although in an alternative embodiment, they may be the same.

The first compensated mask frame is used as the input to a further subtraction unit 307 (or further subtractor). The output of this subtraction results in the subsequent image B.

In mathematical terms, considering an input of the sequence of X-ray images I, of which $I_t$ is a current frame, $I_{t0}$ is a non-contrast frame before a first registration, F(.) and J(.) are operators denoting the first and second registration transforms, $A_T$ is an intermediate image sequence, $A_{t1}$ is an independent frame of the intermediate image sequence, and $B_T$ is a subsequent image frame, the operation being implemented is:

$$A_T = I_t - F(I_{t0}) \quad (1)$$

$$B_T = A_t - J(A_{t1}) \quad (2)$$

As noted by the variable index $t_0$ and $t_1$, searches in the F and J operators may use different frame indexes to each other to achieve the best registration match for each stage of the algorithm.

Figure 4:
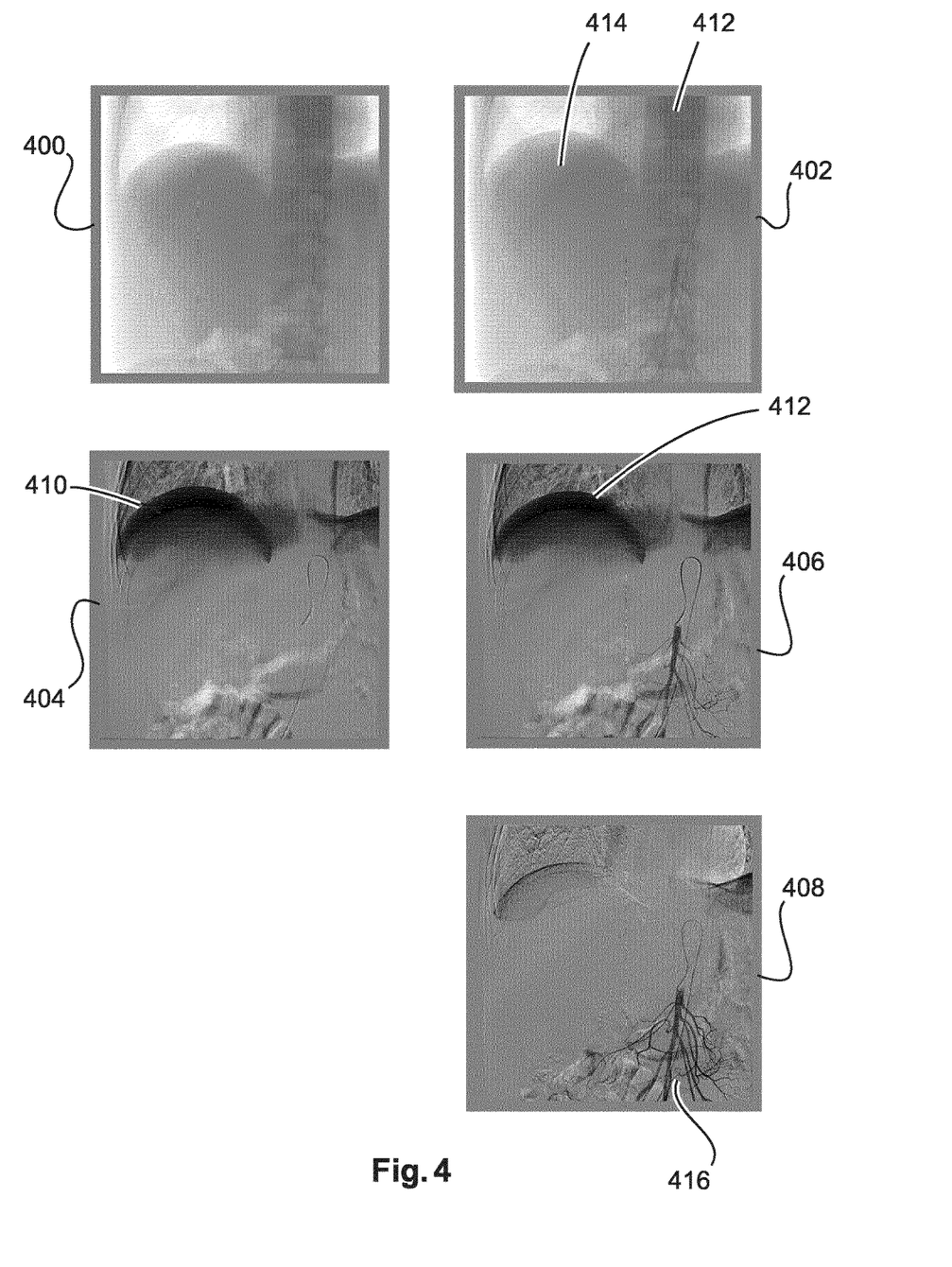
FIG. 4 shows typical results when the algorithm is applied.

FIG. 4 shows five images representing stages of the algorithm, as applied to X-ray data of a patient's thorax. A frame 400 is a non-contrast frame image obtained before the injection of a contrast agent into a region of interest of a patient. A frame 402 is a contrast frame acquired after the injection of a contrast agent into the region of interest of a patient. This injection occurs in the thoracic region, and the trace of a spinal column and the top of the lungs is visible in the frames 400 and 402. The presence of the contrast agent after injection is only dimly visible in the frame 402.

Intermediate frame 406 already shows an improved region or the vasculature containing contrast agent. In this experimental example, the first iteration of the algorithm has removed the spinal column. This is advantageous because the contrast agent is injected into a region obscured by the spine. It will be seen that the subtracted mask and subtracted frame from the first stage has a large black region, indicated with references 410 and 412. This is a motion artefact caused by the motion of lung tissue between the capture of the mask frame and the contrast frame.

The lung tissue is in a second layer of a region of interest. Therefore, the second stage of the algorithm generates a compensated mask frame 404, and when this is subtracted from the intermediate frame 406, a subsequent image 408 results. In this image, a stationary and rigid spine 412 and a moving lung tissue artefact 414 have been substantially removed from the frame, leaving only the vasculature, containing the contrast agent, at 416.

Therefore, it can be seen from this result that the application of this algorithm results in a superior digital subtraction angiogram when more than one moving (or stationary) layers are present.

According to an embodiment of the invention, an example of the method as described above is provided, which further comprises the steps of:

b1) generating a first plurality of geometrical transforms; and b2) concatenating the plurality of non-contrast frames $I_M$ and/or contrast frames $I_C$ with additional non-contrast frames and/or contrast frames, transformed according to geometrical transforms in the first plurality of geometrical transforms.

According to this embodiment, the generation of the first variety of geometrical transforms may comprise any rigid or non-rigid geometrical transformation within the space of possible transformations of the frames of the X-ray image sequence.

In an embodiment, the space of potential geometrical transforms may be sampled in order to reduce computational complexity.

In step b2), the original X-ray image sequence is extended by adding additional frames to it, which have been transformed according to the geometrical transforms in the first variety of geometrical transforms.

In an embodiment, all X-ray image sequence frames may be transformed by all geometrical transforms, and concatenated to the original variety of mask frames and/or contrast frames.

Various techniques for reducing computational complexity, such as randomly sampling the two-dimensional space of X-ray image sequence frames and geometrical transforms may be applied, as defined above. Alternatively, geometrical transforms likely to lead to negligible utility in the identification of a suitable contrast and/or mask frame for registration may be filtered out before registration (for example, if the geometrical transform of the X-ray image sequence is too oblique or too distended).

The purpose of concatenating the plurality of mask frames and/or contrast frames with such a set of transformations is that it is possible to optimize the similarity of the layer image content of the contrast frame used for motion vector field estimation in comparison to the mask frames. Therefore, the first compensated mask frame to compensate the motion in the first layer or a second layer of the region of interest may be generated more accurately.

According to an embodiment of the invention, an example of the method is provided as described previously, wherein in step b) the generation of the first compensated mask frame $MA_{t0}$ comprises:

b3) searching in the plurality of non-contrast frames $I_M$ for a first non-contrast frame $I_{M1}$ having a first layer with a similar layer image content to that of the first contrast frame $I_t$; and b4) applying a first registration between the first non-contrast frame $I_{M1}$ and the first contrast frame $I_t$ to generate the first compensated mask frame.

According to this embodiment, when the first compensated mask frame is generated, a search is made for a first layer of the region of interest, which is most similar in image content to that of the first contrast frame $I_t$. Because the frame identified is most similar, it will require a less radical registration between the first non-contrast frame and the first contrast frame, leading to a better quality, and a reduction in computational complexity.

It will be noted that the previous embodiment can be applied to a search in a plurality of non-contrast frames in the X-ray image sequence as a sequential input only, or it may be applied to the concatenated plurality of non-contrast frames and/or contrast frames as described previously.

According to an embodiment of the invention, during the step b3) of searching in the plurality of contrast frames for a first contrast frame having a first layer with a similar image content to that of the first contrast frame, the region of the contrast frame, which is accessed for identifying a similar layer image content, is a portion of the frame, which lies outside the region with any contrast agent injected. Advantageously, this avoids a misregistration owing to the fact that the contrast agent itself interferes with the search process.

According to this embodiment, an extra image processing stage (such as a recognition of areas with high contrast) is applied to the contrast frames $I_C$ so that the region of the contrast frames affected by contrast agent are denoted as not useful for use as a region of the contrast frame, which is accessed for identifying a similar layer image content.

According to an embodiment of the invention, a method as previously described is provided, further comprising the steps of:

d1) generating a second plurality of geometrical transforms; and d2) and to concatenate a sequence of the results of the subtraction of the first compensated mask frame ($MA_{t0}$) from the contrast frame ($I_t$), with additional frames of the sequence, wherein the additional frames of the intermediate image sequence are transformed according to geometrical transforms in the plurality of geometrical transforms.

As discussed above in relation to the first stage of the algorithm, the second stage of the algorithm concerned with removing motion in the second layer of the region of interest can also benefit from increasing the search space during the generation of the second compensated mask frame by, applying a plurality of geometrical transforms to the intermediate image sequence A, and then concatenating the original intermediate image sequence to the transformed intermediate images.

According to an embodiment of the invention, a method is provided as described previously, wherein in step d) the generation of the second compensated mask frame $MB_{t1}$ comprises:

d3) searching an intermediate image sequence A for a second non-contrast frame $A_{t1}$ having a second layer with a similar layer image content with that of the intermediate frame ($A_t$); and d4) applying a second registration between the second non-contrast frame $A_{r1}$ and the intermediate frame $A_r$ for generating the second compensated mask frame.

According to an embodiment of the invention, a method is provided as discussed above, wherein the layer image content is one of, or a combination of, intensity, gradient, pattern, texture, contour, noise-figure, or a shape.

According to this embodiment, many different parameters may be applied in the identification of images during the registration process. A brief inspection of the images of FIG. 4 reveals that many different image attributes could be used during the registration process. The upper lobes of the lung artefacts 410, for example could be used to identify the lung shape in the X-ray frames 404 and/or 406 parametrically. Layer image content in the intermediate image sequence of the frames 404 and 406 is more textured at the top, and this could also be used to improve the registration.

According to an embodiment of the invention, a method is provided as discussed above, wherein in steps b) and/or d), the searching in the plurality of non-contrast frames $I_M$ and/or an intermediate image sequence A is performed using a parametric search. Such a method allows for the precise specification of the model of motion used for compensation. Limiting the class of motions used for compensation is often important for improving the estimation robustness, provided that the assumed class does fit with reality.

For instance, for breathing compensation, a translational motion model along the direction of the spine (a vertical direction in the images of FIG. 4) is often a good choice, that achieves a useful compromise between robustness and accuracy.

Therefore, it will be seen that a digital subtraction angiography method is presented, which can allow the removal of two or more independent motion layers inside a region of interest.

The registration algorithms applied to the removal of the different motion layers may be varied, dependent on the motion characteristics of a certain layer. In the case that the layer to be removed is a spine or bone, such structures are relatively rigid. Therefore, an identity registration can be applied. This is possible, because there is zero motion, or substantially zero motion, of the spinal column, between frames, unless the patient is moved on the fluoroscopy table during the examination. Bones of the rib cage may experience slightly more motion, owing to thoracic movement during breathing.

A parametric registration algorithm may be applied to distinctive shapes in the region of interest. For example, the diaphragm and the lobes of the lung have a relatively predictable outline, which changes in a predictable manner during breathing. A parametric equation can thus be derived to represent the diaphragm of lung position simply.

As discussed above, for the removal of breathing layers (such as the lungs and connected tissue), an image-wise vertical translation algorithm (a translation in an orientation parallel to the left image border, for example) may be applied, because during breathing, the lung tissue is substantially moved along the spinal column.

For complex motions, such as motions in the stomach or bowel area, layer movement can be represented using a more complicated algorithm, such as an elastic (non-rigid) registration algorithm.

According to an embodiment of the invention, in steps b3) or d3), the detection of the similarity of the layer image content is performed using a method selected from the group of: (i) a grey scale range search metric, (ii) a gradient metric, (iii) a texture shape metric, and (iv) a contour similarity layer image metric. Alternatively, the metric could be a log-transformed similarity measure.

Advantageously, this means that the detection of layer movement in the X-ray frames or intermediate frames of the algorithm may be customised for each layer that the algorithm is applied to. This enables more effective selection of frames to use in the registration of each layer, increasing registration effectiveness.

For example, when removing a bone layer, it could be appropriate to apply the grey scale range search metric or a gradient metric to the image frame. A texture shape or contour similarity layer image metric may be more effective to deduce tissue layer movement.

Therefore, it will be taken from the preceding discussion that multiple independent layers may be identified, and removed from a digital subtraction angiogram based on the optical and/or bio-mechanical characteristics of those layers, independently of the other layers.

According to an embodiment of the invention, a method is provided as described above, wherein the first layer of the region of interest is a rigid layer.

According to an embodiment of the invention, a method is provided as described above, wherein the generation of the first compensated mask frame and the second compensated mask frame each uses a different algorithm wherein each algorithm is specific to the first or second layer.

As described above, the use of a different registration algorithm and/or a different algorithm detection of the similarity of the layer image content, for different motion layers, results in a better removal of artefacts resulting from different layers.

According to an embodiment of the invention, a method is provided, wherein in step b) the first layer is a rigid layer, and/or wherein in step d) the second layer is a layer associated with patient breathing motions.

According to an embodiment of the invention, a method for providing a digital subtraction angiogram, is provided comprising the following steps:

a) acquiring 100 an X-ray image sequence I comprising: (i) a plurality of non-contrast frames ($I_M$), acquired without the injection of a contrast agent into the region of interest, and (ii) a plurality of contrast frames $I_C$ acquired after the injection of a contrast agent into the region of interest;

b) generating 102 a first compensated mask frame $MA_{r0}$; wherein the first compensated mask frame compensates for a motion in a first layer of the region of interest; and wherein the motion in the first layer occurs in the time between the acquisition of the plurality of non-contrast frames $I_M$ and the plurality of contrast frames $I_C$;

c) subtracting 104 the first compensated mask frame $MA_{r0}$ from a first contrast frame of the plurality of contrast frames $I_t$, to derive an intermediate frame $A_t$ of an intermediate image sequence A;

d) generating 106 a second compensated mask frame $MB_{r1}$ selected from an intermediate frame $A_{r1}$ of the intermediate image sequence A; wherein the second compensated mask frame compensates for a motion of a second layer of the region of interest; and wherein the motion in the second layer occurs in the time between the acquisition of the plurality of non-contrast frames $I_M$ and plurality of contrast frames $I_C$;

e) subtracting 108 the second compensated mask frame $MB_{r1}$ from the intermediate frame $A_{r1}$ of the intermediate image sequence A, to derive a subsequent image ($B_t$); and f) displaying 110 the subsequent image $B_t$.

Figure 5:
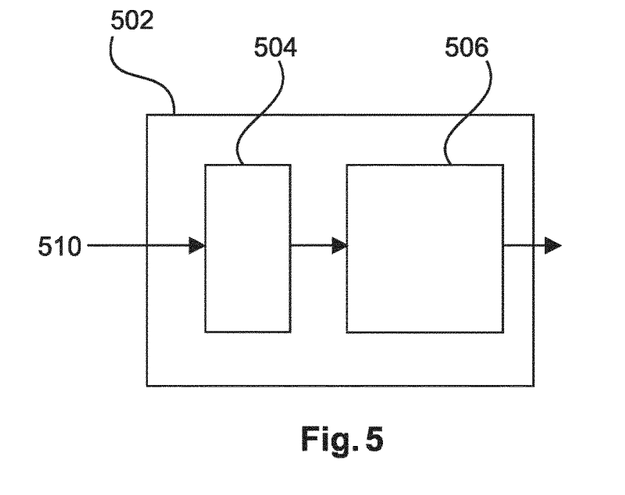
FIG. 5 shows a device according to an aspect of the invention.

According to an aspect of the invention, there is provided a device 502 for providing a digital subtraction angiogram, comprising:

an interface unit 504; and a processing unit 506.

The interface unit is configured to provide a non-contrast frame $I_M$ for use as a mask image, and to provide a contrast frame $I_t$, wherein the non-contrast frame and the contrast frame are acquired from a frame sequence of a region of interest of a patient.

The processing unit is configured to generate a first compensated mask frame $MA_{t0}$ by compensating the non-contrast frame $I_M$ for motion occurring in a first layer of the region of interest; to subtract the first compensated mask frame from the contrast frame $I_t$; to generate a second compensated mask frame $MB_{t1}$ by compensating the first compensated mask frame $MA_{t0}$ for motion occurring in a second layer of the region of interest; and to generate a subsequent image $B_t$ by subtracting the second compensated mask frame from the result of the subtraction of the first compensated mask frame $MA_{t0}$ from the contrast frame $I_t$.

According to an embodiment of the invention, an output unit 508 is further configured to display the subsequent image.

FIG. 5 shows an exemplary device 502 for providing a digital subtraction angiogram. It will be appreciated that many implementation methods exist to provide such a device, such as a personal computer, a graphics accelerator of a personal computer, a digital signal processor, a field programmable gate array or other programmable logic, a microprocessor, an application specific integrated circuit, or any other combination of these, or equivalents.

According to an embodiment of the invention, a device as described above is provided, wherein the first layer is a rigid layer, and the second layer is a layer associated with patient breathing motions.

According to an embodiment of the invention, a device as described above is provided, wherein the processing unit is configured to generate the first compensated mask frame $MA_{t0}$ and the second compensated mask frame $MB_{t1}$ using a different algorithm, wherein each algorithm is specific to the first or second layer. According to an embodiment of the invention, a device is provided as described above, wherein the processing unit 506 is further configured to generate a first plurality of geometrical transforms, and to concatenate a plurality of non-contrast frames $I_M$ and/or contrast frames $I_C$ with additional non-contrast frames and/or contrast frames, wherein the additional non-contrast frames and/or contrast frames are transformed according to the geometrical transforms in the first plurality of geometrical transforms.

According to an embodiment of the invention, a device is provided as described above, wherein the processing unit 506 is further configured to generate the first compensated mask frame $MA_{t0}$ by searching in the plurality of non-contrast frames $I_M$ for a first non-contrast frame $I_{M1}$ having a first layer with a similar layer image content to that of the first contrast frame $I_t$, and by applying a first registration between the first non-contrast frame $I_{M1}$ and the first contrast frame $I_t$ to generate the first compensated mask frame.

According to an embodiment of the invention, the processing unit 506 is further configured to generate a second plurality of geometrical transforms, and to concatenate a sequence of the results of the subtraction of the first compensated mask frame $MA_{t0}$ from the contrast frame $I_t$, with additional frames of the sequence. The additional frames of the intermediate image sequence are transformed according to geometrical transforms in the plurality of geometrical transforms.

According to an embodiment of the invention, a device is provided as described above, wherein the processing unit 506 is further configured to search in the sequence of results of the subtraction of the first compensated mask frame $MA_{t0}$ from the contrast frame $I_t$ for a second intermediate frame $A_{t1}$ having a second layer with a similar layer image content to that of the result of the subtraction of the first compensated mask frame $MA_{t0}$ from the contrast frame $I_t$. The processing unit is configured to apply a second registration between the second result of the subtraction of the first compensated mask frame $MA_{t0}$ from the contrast frame $I_t$ frame and the result of the subtraction of the first compensated mask frame $MA_{t0}$ from the contrast frame $I_t$.

According to an embodiment of the invention, a device is provided as described above, wherein the layer image content is one of, or a combination of, an intensity, gradient, pattern, texture, contour, noise figure, a motion content of the layer, or a shape of the first or second layer.

According to an embodiment of the invention, a device is provided as described above, wherein the generation of the first compensated mask frame and the second compensated mask frame each use a different algorithm wherein each algorithm is specific to the first or second layer.

According to an embodiment of the invention, a device is provided as described above, wherein the first layer of the region of interest is a rigid layer.

According to an embodiment of the invention, a device is provided as described above, wherein the second layer of the region of interest is a tissue layer, which moves in synchrony with a patient's breathing, or a patient's cardiac motion.

According to an embodiment of the invention, a device is provided as described above, wherein the searching in the plurality of non-contrast frames I and/or in the intermediate image sequence A is performed using a parametric search.

Figure 6:
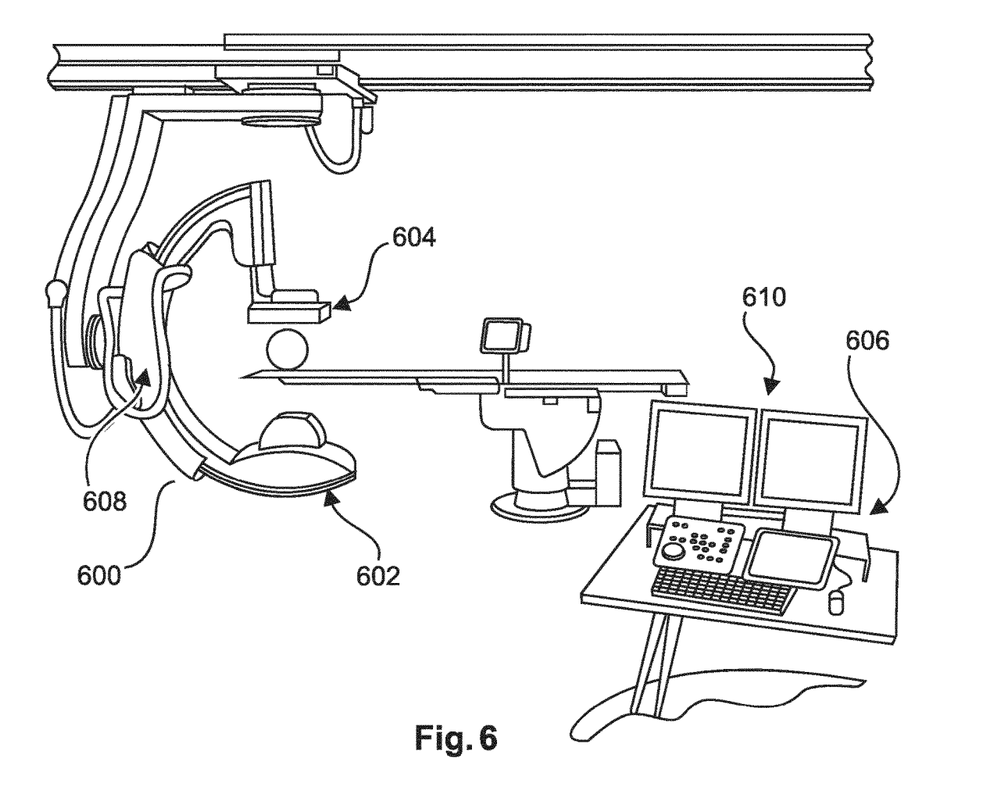
FIG. 6 shows an X-ray imaging arrangement according to an aspect of the invention.

According to an aspect of the invention, as shown in FIG. 6, an X-ray imaging arrangement 600 is provided. The arrangement comprises an X-ray acquisition device 608, with an X-ray source 602 and an X-ray detector 604, and a device for providing a digital subtraction algorithm 606 as described previously, as indicated with 606.

The X-ray image acquisition device 608 is configured to acquire image data of the chest of the patient from the X-ray detector 604, and to provide the image data to the interface of the device for providing a digital subtraction angiogram.

According to an aspect of the invention, there is provided a computer program element for controlling a device as previously described, which, when the computer program element is executed by a processing unit, is adapted to perform the method steps as previously described.

According to an aspect of the invention, there is provided a computer readable medium having stored the program element described previously.

A computer program element might therefore be stored on a computer unit, which might also be part of an embodiment of the present invention. This computing unit may be adapted to perform or induce performance of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention.

A computer program may be stored and/or distributed on a suitable medium, such as optical storage media or a solid state medium supplied together with, or as a part of other hardware, but may also be distributed in other forms, such as via the Internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to the device-type claims. However, a person skilled in the art will gather from the above, and the following description that, unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for providing a digital subtraction angiogram, the device comprising:
   an interface unit;
   a processing unit; and
   wherein the interface unit is connected to the processing unit and is configured to provide a non-contrast frame ($I_M$) for use as a mask image, and to provide a contrast frame ($I_t$), wherein the non-contrast frame and the contrast frame are acquired from a frame sequence of a region of interest of a patient;
   wherein the processing unit is configured to generate a first compensated mask frame ($MA_{r0}$) by compensating the non-contrast frame ($I_M$) for motion occurring in a first layer of the region of interest; to subtract the first compensated mask frame from the contrast frame ($I_t$); to generate a second compensated mask frame ($MB_{t1}$) by compensating the first compensated mask frame ($MA_{r0}$) for motion occurring in a second layer of the region of interest; and to generate a subsequent image ($B_t$) by subtracting the second compensated mask frame from a result of the subtraction of the first compensated mask frame ($MA_{r0}$) from the contrast frame ($I_t$).

2. The device according to claim 1, wherein the first layer is a rigid layer, and the second layer is a layer associated with patient breathing motions.

3. The device according to claim 1, wherein the processing unit is configured to generate the first compensated mask frame ($MA_{r0}$) and the second compensated mask frame ($MB_{t1}$) using a different algorithm, wherein each algorithm is specific to the first or second layer.

4. The device according to claim 1, wherein the processing unit is further configured to generate a first plurality of geometrical transforms, and to concatenate a plurality of non-contrast frames ($I_M$) and/or contrast frames ($I_t$) with additional non-contrast frames and/or contrast frames, wherein the additional non-contrast frames and/or contrast frames are transformed according to the geometrical transforms in the first plurality of geometrical transforms.

5. The device according to claim 4, wherein the processing unit is further configured to generate the first compensated mask frame ($MA_{r0}$) by searching in the plurality of non-contrast frames ($I_M$) for a first non-contrast frame ($I_{M1}$) having a first layer with a similar layer image content to that of the first contrast frame ($I_t$), and by applying a first registration between the first non-contrast frame ($I_{M1}$) and the first contrast frame ($I_t$), to generate the first compensated mask frame.

6. The device according to claim 1, wherein the processing unit is further configured to generate a second plurality of geometrical transforms, and to concatenate a sequence of the results of the subtraction of the first compensated mask frame ($MA_{r0}$) from the contrast frame ($I_t$), with additional frames of the sequence to produce additional frames of an intermediate image sequence; and
   wherein the additional frames of the intermediate image sequence are transformed according to geometrical transforms in the second plurality of geometrical transforms.

7. The device according to claim 1, wherein the processing unit is further configured to search in a sequence of results of the subtraction of the first compensated mask frame ($MA_{r0}$) from the contrast frame ($I_t$) for a second intermediate frame ($A_{t1}$) having a second layer with a similar layer image content to that of the result of the subtraction of the first compensated mask frame ($MA_{r0}$) from the contrast frame ($I_t$) ($At_1$), and to apply a second registration between a second result of the subtraction of the first compensated mask frame ($MA_{r0}$) from the contrast frame ($I_t$) frame ($A_{t1}$) and the result of the subtraction of the first compensated mask frame ($MA_{r0}$) from the contrast frame ($I_t$).

8. The device according to claim 1, wherein the layer image content is one of, or a combination of, an intensity, gradient, pattern, texture, contour, noise figure, a motion content of the layer, or a shape of the first or second layer.

9. The device according to claim 1, wherein the first layer of the region of interest is a rigid layer and/or the second layer of the region of interest is a tissue layer associated with patient breathing motions.

10. An X-ray imaging arrangement, comprising:
an X-ray acquisition device with an X-ray source and an X-ray detector;
a device for providing a digital subtraction algorithm according to claim 1; and
a display device;
wherein the X-ray imaging arrangement is configured to acquire X-ray image data of a region of interest of a patient, and to provide the X-ray image data to the interface unit of the device for providing a digital subtraction angiogram, and to display the digital subtraction angiogram on the display device.

11. A method for providing a digital subtraction angiogram, the method comprising acts of:
providing a non-contrast frame ($I_M$) for use as a mask image, and providing a contrast frame ($I_t$), wherein the non-contrast frame and the contrast frame are acquired from a frame sequence (I) of a region of interest of a patient;
generating a first compensated mask frame ($MA_{t0}$) by compensating the non-contrast frame ($I_M$) for motion occurring in a first layer of the region of interest;
subtracting the first compensated mask frame ($MA_{t0}$) from the contrast frame ($I_t$);
generating a second compensated mask frame ($MB_{t1}$) by compensating the first compensated mask frame ($MA_{t0}$) for motion occurring in a second layer of the region of interest; and
generating a subsequent image ($B_t$) by subtracting the second compensated mask frame from the result of the subtraction of the first compensated mask frame ($MA_{t0}$) from the contrast frame ($I_t$).

12. The method according to claim 11, wherein the first layer is a rigid layer, and/or wherein the second layer is a layer associated with patient breathing motions.

13. The method according to claim 11, wherein the generation of the first compensated mask frame and the second compensated mask frame each uses a different algorithm, wherein each algorithm is specific to the first layer or the second layer.

14. A non-transitory computer readable medium comprising computer instructions which, when executed by a processing unit, configure the processing unit to perform a method for providing a digital subtraction angiogram, the method comprising acts of:
providing a non-contrast frame ($I_M$) for use as a mask image, and providing a contrast frame ($I_t$), wherein the non-contrast frame and the contrast frame are acquired from a frame sequence (I) of a region of interest of a patient;
generating a first compensated mask frame ($MA_{t0}$) by compensating the non-contrast frame ($I_M$) for motion occurring in a first layer of the region of interest;
subtracting the first compensated mask frame ($MA_{t0}$) from the contrast frame ($I_t$);
generating a second compensated mask frame ($MB_{t1}$) by compensating the first compensated mask frame ($MA_{t0}$) for motion occurring in a second layer of the region of interest; and
generating a subsequent image ($B_t$) by subtracting the second compensated mask frame from the result of the subtraction of the first compensated mask frame ($MA_{t0}$) from the contrast frame ($I_t$).

\* \* \* \* \*